United States Patent
Wang

(10) Patent No.: US 11,511,263 B2
(45) Date of Patent: Nov. 29, 2022

(54) METHODS FOR PRODUCING LONG-CHAIN HYDROCARBON MOLECULES USING HEAT SOURCE

(71) Applicant: BEIJING GUANGHE NEW ENERGY TECHNOLOGY CO., LTD., Beijing (CN)

(72) Inventor: Cong Wang, Beijing (CN)

(73) Assignee: Beijing Guanghe New Energy Technology Co., Ltd., Beijing (CN)

( * ) Notice: Subject to any disclaimer, the term of this patent is extended or adjusted under 35 U.S.C. 154(b) by 0 days.

(21) Appl. No.: 17/286,033

(22) PCT Filed: Oct. 18, 2018

(86) PCT No.: PCT/CN2018/110766
§ 371 (c)(1),
(2) Date: Apr. 16, 2021

(87) PCT Pub. No.: WO2020/077581
PCT Pub. Date: Apr. 23, 2020

(65) Prior Publication Data
US 2021/0379570 A1    Dec. 9, 2021

(51) Int. Cl.
| | | |
|---|---|---|
| C07C 1/10 | (2006.01) | |
| C10G 2/00 | (2006.01) | |
| B01J 23/75 | (2006.01) | |
| B01J 35/00 | (2006.01) | |
| B01J 35/02 | (2006.01) | |
| C07C 1/12 | (2006.01) | |

(52) U.S. Cl.
CPC ............ *B01J 23/75* (2013.01); *B01J 35/0013* (2013.01); *B01J 35/023* (2013.01); *C07C 1/10* (2013.01); *C07C 1/12* (2013.01); *C10G 2/331* (2013.01); *C10G 2/332* (2013.01); *C10G 2/40* (2013.01); *C07C 2523/75* (2013.01); *C10G 2300/4006* (2013.01); *C10G 2300/70* (2013.01)

(58) Field of Classification Search
None
See application file for complete search history.

(56) References Cited

U.S. PATENT DOCUMENTS

| | | | | |
|---|---|---|---|---|
| 2004/0029983 A1* | 2/2004 | Yakobson | ............... | C10K 1/101 |
| | | | | 518/703 |
| 2012/0097521 A1 | 4/2012 | Shen et al. | | |
| 2013/0168228 A1* | 7/2013 | Ozin | .................... | B01J 23/755 |
| | | | | 204/157.9 |

FOREIGN PATENT DOCUMENTS

| | | | | |
|---|---|---|---|---|
| CN | 108620089 A | 10/2018 | | |
| WO | WO1997009293 A1 * | 3/1997 | ............ | C07C 27/00 |
| WO | 2013/063052 A1 | 5/2013 | | |
| WO | 2017/040355 A1 | 3/2017 | | |
| WO | 2017/120740 A1 | 7/2017 | | |

OTHER PUBLICATIONS

Hemalatha, K. et al. "Function of Nanocatalyst in Chemistry of Organic Compounds Revolution: An Overview" Journal of Nanomaterials vol. 2013, Article ID 341015, 23, pp. 1-24 (Year: 2013).*
Translation of Patent No. CN108620089B, Oct. 9, 2018, pp. 1-14 (Year: 2018).*
Wang, Y. et al. "Highly Active Supported Pt Nanocatalysts Synthesized by Alcohol Reduction towards Hydrogenation of Cinnamaldehyde: Synergy of Metal Valence and Hydroxyl Groups" Chem. Asian J. 2015, 10, 1561-1570 (Year: 2015).*
Varghese, O. K. et al. "High-Rate Solar Photocatalytic Conversion of CO2 and Water Vapor to Hydrocarbon Fuels" Nano Lett., 2009, vol. 9, No. 2, 731-737 (Year: 2009).*
Wang, C. et al. "Using metal nanostructures to form hydrocarbons from carbon dioxide, water and sunlight" AIP Advances 2011, 1, 042124 (Year: 2011).*

* cited by examiner

*Primary Examiner* — Medhanit W Bahta
(74) *Attorney, Agent, or Firm* — Morgan, Lewis & Bockius LLP

(57) ABSTRACT

Provided is a method for producing organic molecules having at least two carbon atoms chained together by the reaction of a hydrogen-containing source, a carbon-containing source and an optional nitrogen-containing source in the presence of a nanostructure or nanostructures, wherein the reaction is initiated by heat.

14 Claims, 5 Drawing Sheets

METHODS FOR PRODUCING LONG-CHAIN HYDROCARBON MOLECULES USING HEAT SOURCE

FIELD OF THE INVENTION

The invention generally relates to carbon dioxide sequestration and renewable energy. More particularly, the invention relates to nanoparticle catalysts and methods for producing long chain hydrocarbon molecules using heat source.

BACKGROUND

Carbon emissions contribute to climate change, which can have serious consequences for humans and the environment. Many endeavors were made in order to capture, utilize, and non-atmospheric sequester the carbon dioxide emitted from fossil fuel-fired electric power plants and industrial plants. Some technologies have shown great promise in this area but are still long way from demonstrating on a commercial scale, it is a priority to establish technical, environmental, and economic feasibility of large-scale capture and disposal of carbon dioxide from industrial plants.

Conventional approach for carbon dioxide sequestration is generally directed to artificial photosynthesis using sunlight as the energy source. Most efforts so far are devoted for the development of catalysts, but the solar-to-chemical efficiencies are typically 1 or 2 orders of magnitude lower than natural photosynthesis, which is lacking of efficiency for industrial application.

Industrial plants produce a huge amount of gaseous emission which carries carbon-containing materials and latent heat. It is of great interest for recycling the material and heat energy contained in the emission waste.

SUMMARY OF THE INVENTION

Herein, the inventors have demonstrated a novel artificial carbon sequestration technology which provided a unique method for producing long-chain organic molecules by utilizing CO or $CO_2$ from industrial flue gas or atmosphere in the presence of nanostructure catalysts using heat source.

One aspect of the present invention relates to a method for producing organic molecules having at least two carbon atoms chained together by the reaction of a hydrogen-containing source, a carbon-containing source and an optional nitrogen-containing source in the presence of a nanostructure or nanostructures, wherein the reaction is initiated by heat.

In certain embodiments, the nanostructure each independently comprises a metal selected from the group consisting of Au, Al, Ag, Mn, Cu, Co, Fe, Ni, Ti, stainless steel and any combination thereof.

In other embodiments, the nanostructure each independently comprises a first component, a second component or any combination thereof, wherein the first component is selected from the group consisting of Mn, Co, Fe, Al, Ag, Au, Pt, Cu, Ni, Zn, Ti, C and any combination thereof, the second component is selected from the group consisting of Mn, Co, Ag, Fe, Ru, Rh, Pd, Os, Ir, La, Ce, Cu, Ni, Ti, oxides thereof, hydroxides thereof, inorganic acid salts thereof, C, and any combination thereof. In preferred embodiments, the first component and the second component are in contact with each other or apart from each other by a distance less than about 200 nm.

In certain embodiments, the nanostructure each independently is from about 1 nm to about 3000 nm in length, width or height, and each independently has an aspect ratio of from about 1 to about 20. The nanostructure each independently has a shape of spherical, spike, flake, needle, grass, cylindrical, polyhedral, 3D cone, cuboidal, sheet, hemispherical, irregular 3D shape, porous structure or any combinations thereof.

In certain embodiments, multiple nanostructures are arranged in a patterned configuration, in a plurality of layers, on a substrate, or randomly dispersed in a medium.

In certain embodiments, the organic molecules comprise saturated, unsaturated and aromatic hydrocarbons, carbohydrates, amino acids, polymers, or a combination thereof.

In certain embodiments, the heat provides a reaction temperature of between about 50° C. and about 800° C. The heat is input externally into the reaction or is inherently carried by one or more of the hydrogen-containing source, the carbon-containing source and the optional nitrogen-containing source.

In certain embodiments, the reaction is initiated by heat in a dark environment. After the reaction is initiated, the reaction is progressed under a light radiation intensity below 1000 $W/m^2$.

In certain embodiments, the carbon-containing source is selected from the group consisting of $CO_2$, CO, $C_{1-4}$ hydrocarbons, $C_{1-4}$ synthesis gas, bicarbonate salts and any combination thereof, or industrial flue gas, exhausts or emissions comprising one or more of these carbon-containing sources.

In certain embodiments, the hydrogen-containing source is selected from the group consisting of water, $H_2$, $C_{1-4}$ hydrocarbons, $C_{1-4}$ alcohols and any combination thereof in liquid or gaseous phase, or waste water, industrial flue gas, exhausts or emissions comprising one or more of these hydrogen-containing sources.

In certain embodiments, the nitrogen-containing source is selected from the group consisting of $N_2$, air, ammonia, nitrogen oxides, nitro compounds, $C_{1-4}$ amines and any combination thereof in liquid or gaseous phase, or air, industrial flue gas, exhausts or emissions comprising one or more of these nitrogen-containing sources.

DETAILED DESCRIPTION

Figure 1:
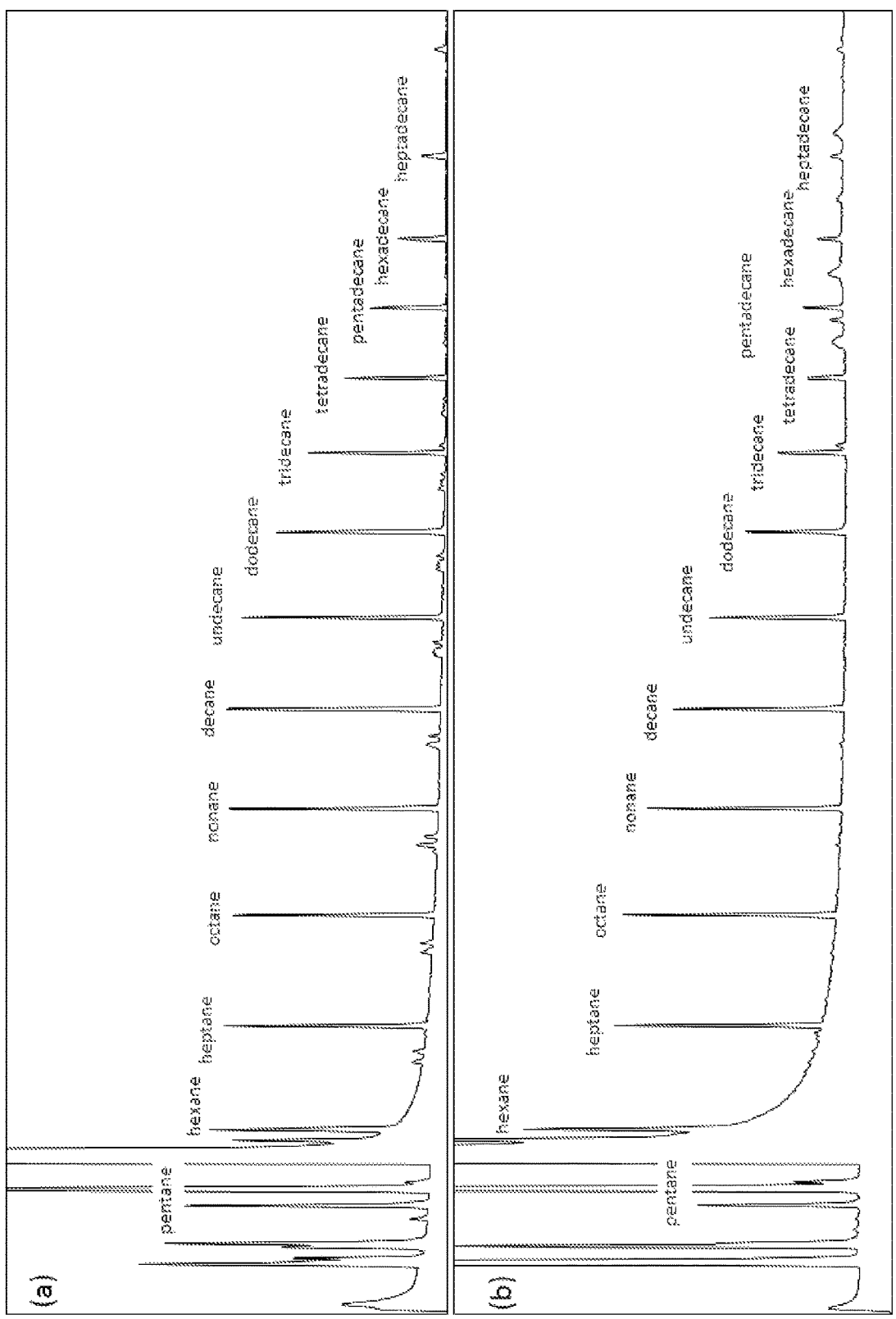
FIG. 1. Gas chromatography of hydrocarbons produced with $^{12}CO_2$ and $^{13}CO_2$ after 20 h of heating.

The invention has demonstrated that, surprisingly and unexpectedly, artificial carbon sequestration can be achieved in the presence of nanostructure catalysts using heat source as the sole mean for initiating and maintaining the reaction to produce long-chain organic molecules from a hydrogen-containing source, a carbon-containing source and an optional nitrogen-containing source.

Before further description of the present invention, certain terms employed in the specification, examples and appended claims are defined in the following section. The definitions listed herein should be read in light of the remainder of the disclosure and understood as by a person of skill in the art.

Unless defined otherwise, all technical and scientific terms used herein have the same meaning as commonly understood by a person of ordinary skill in the art to which this invention belongs.

Nanostructure Catalyst

Nanostructure catalyst is used in the reaction of the present invention for the initiation of the reaction by using heat source.

Without wishing to be bound by theory, the nanostructure catalyst of the present invention interacts with the raw materials of the reaction to reduce the activation energy of the reaction so as to initiate the reaction by Utilizing thermal energy. The catalyst of the present invention may exhibit a temperature-dependent property in the catalysis behavior. The term "temperature-dependent" used herein refers to properties that may vary when temperature changes by a given level. The temperature difference to alter the property may be any degrees, such as 0.1° C., 1° C., 5° C., 10° C., 20° C., 50° C., or 100° C. In certain embodiment, the product of the catalyzed reaction of the present invention is temperature-dependent.

The term "nanostructure" used herein refers to a structure having at least one dimension within nanometer range, i.e. 1 nm to 1000 nm in at least one of its length, width, and height. Nanostructure can have one dimension which exceeds 1000 nm, for example, have a length in micrometer range such as 1 micron to 5 micron. In certain cases, tubes and fibers with only two dimensions within nanometer range are also considered as nanostructures. Material of nanostructure may exhibit size-related properties that differ significantly from those observed in bulk materials.

The nanostructure of the present invention each independently comprises a metal selected from the group consisting of Mn, Au, Al, Ag, Cu, Co, Fe, Ni, Ti, stainless steel and any combination thereof, preferably Co, or the nanostructure each independently comprises a first component, a second component or any combination thereof, wherein the first component is selected from the group consisting of Mn, Co, Fe, Al, Ag, Au, Pt, Cu, Ni, Zn, Ti, C and any combination thereof, preferably selected from the group consisting of Mn, Co, Ag, Au, C, and any combination thereof, the second component is selected from the group consisting of Mn, Co, Ag, Fe, Ru, Rh, Pd, Os, Ir, La, Ce, Cu, Ni, Ti, oxides thereof, hydroxides thereof, inorganic acid salts thereof, C, and any combination thereof, preferably selected from the group consisting of Co, Fe, Cu, Ni, oxides thereof and any combination thereof.

The nanostructure of the present invention each independently is from about 1 nm to about 3000 nm in length, width or height. The length thereof is preferably from about 100 nm to about 3000 nm, more preferably from about 500 nm to about 2500 nm, yet more preferably from 1000 nm, to about 2000 nm. The width or height thereof is preferably from about 1 nm to about 1000 nm, more preferably from about 100 nm to about 800 nm, yet more preferably from about 200 nm to about 500 nm.

The nanostructure of the present invention each independently has an aspect ratio (i.e., length to width/height ratio) of from about 1 to about 20, from about 1 to about 10, or from about 2 to about 8. The nanostructure of the present invention can also have a relatively aspect ratio such as from about 1 to about 2.

The nanostructure of the present invention each independently has a shape of spherical, spike, flake, needle, grass, cylindrical, polyhedral, 3D cone, cuboidal, sheet, hemispherical, irregular 3D shape, porous structure or any combinations thereof.

Multiple nanostructures of the present invention can be arranged in a patterned configuration, in a plurality of layers, on a substrate, or randomly dispersed in a medium. For example, nanostructures may be bound to a substrate. In such case, the nanostructures are generally not aggregated together, but rather, pack in an orderly fashion. Alternatively, multiple nanostructures can be dispersed in a fluid medium, in which each nanostructure is free to move with respect to any other nanostructures.

In present invention catalyst having a nanostructure or nanostructures is preferably used in the reaction for producing organic molecules having at least two carbon atoms chained together.

Catalyst in the Form of a Nanostructure

In certain embodiment, catalyst of the present invention has a form of a nanostructure. The nanostructure may have any suitable geometry and dimensions. For example, the nanostructure has a spike or grass-like geometry. Alternatively, the nanostructure has a flake-like geometry having a relatively thin thickness. Preferably, the nanostructure takes on a configuration of a nanoforest, nanograss and/or nanoflake.

The nanostructure may have a relatively high aspect ratio, such nanostructure may adopt a configuration of nano-spike, nano-flake or nano-needle. The aspect ratio can be from about 1 to about 20, from about 1 to about 10, or from about 2 to about 8. Preferably, the length of the nanostructure can be from about 100 nm to about 3000 nm, from about 500 nm to about 2500 nm, or from 1000 nm to about 2000 nm; the width or height can be from about 1 nm to about 1000 nm, from about 100 nm to about 800 nm, or from about 200 nm to about 500 nm.

The nanostructure may be bound to a substrate. Accordingly, the nanostructures are generally not aggregated together, but rather, packed in an orderly fashion. The substrate can be formed of a metal or a polymeric material (e.g., polyimide, PTFE, polyester, polyethylene, polypropylene, polystyrene, polyacrylonitrile, etc.).

The nanostructure each independently comprises a metal selected from the group consisting of Mn, Au, Al, Ag, Cu, Co, Fe, Ni, Ti, stainless steel and any alloy or combination thereof. Preferably, the nanostructure is substantially made of Co. In some embodiments, the nanostructure can comprise a metal oxide coating formed spontaneously or intentionally onto the metal portion. In certain embodiments, a nanostructure can be formed into two or more layers with different element compositions in each layer.

The term "alloy" used herein refers to a mixture of metals or a mixture of metal and other elements. Alloys are defined by metallic bonding character. An alloy may be a solid solution of metal elements (a single phase) or a mixture of metallic phases (two or more phases).

As an example, the catalyst described in patent applications US 2012/0097521 and PCT/US2016/049164 can be used as the catalyst in the form of a nanostructure of the present invention. Said documents are hereby incorporated into the present application by reference in their entirety.

Catalyst in the Form of Nanostructures

In certain embodiment, catalyst of the present invention adopts the form of nanostructures including a first component, a second component or any combination thereof. The first component and the second component provide different properties to the catalyst and function synergistically with each other. In the catalyst, the first component and the second component are in contact with each other or have distance less than 200 nm. If the distance between the first component and the second component are outside aforementioned range, the two components cannot exert the effect in cooperation with each other, thus cannot catalyze the photosynthesis reaction.

The first component is selected from the group consisting of Mn, Co, Fe, Al, Ag, Au, Pt, Cu, Ni, Zn, Ti, C and any alloy or combination thereof, preferably selected from the group consisting of Mn, Co, Ag, Au, C, and any combination thereof. The first component can be a pure substance or a mixture. For efficiency and cost reasons, Co is preferably used as the first component in this invention.

The second component is selected from the group consisting of Mn, Co, Ag, Fe, Ru, Rh, Pd, Os, Ir, Ce, Cu, Ni, oxides thereof, hydroxides thereof, inorganic acid salts thereof, C, and any combination thereof, preferably selected from the group consisting, of Co, Fe, Cu, Ni, oxides thereof and any combination thereof. For example, the inorganic acid salts thereof can be chloride, carbonate and bicarbonate. The second component can also be a pure substance or a mixture. In this invention, Co and oxides of Co are preferably used as the second component.

The first component and the second component can be randomly mixed, or regularly mixed. The first component and the second component are in contact with each other or apart from each other by a distance less than about 200 nm, preferably less than about 100 nm. In preferred embodiments, the two components are provided in one nanostructure, and said nanostructure comprises one chemical element as both the first component and the second component, or alloy of two or more chemical elements each as the first component and the second component. As can be seen, certain elements are capable of functioning as both the first component and the second component. In such cases, the nanostructure comprises a same element, such as Mn, Co, Fe, Cu, Ni, C and the like, or the element and its oxide, chloride, carbonate and bicarbonate, such as Co and CoO, Fe and FeO, etc.

In addition, mixture of different elements will modify the catalysis property of the nanostructures. The nanostructures functions in various states, such as dispersed, congregated, or attached/grew on the surface of other materials. In preferred embodiments, the nanostructures are dispersed in a medium, in which the medium is preferably a reactant of the reaction, such as water.

The nanostructures each independently has a length, width and height from about 1 nm to about 1000 nm, preferably from about 100 nm to about 800 nm, or from about 200 nm to about 500 nm. The shapes of the nanostructures can be spherical, cylinders, polyhedrons, 3D cones, cuboids, sheets, hemisphere, irregular 3D shapes, porous structure and any combinations thereof.

As an example, the catalyst described in patent application PCT/CN2016/070580 can be used as the catalyst in the form of nanostructures of the present invention. Said document is hereby incorporated into the present application by reference in its entirety.

Reaction Initiation by Heat

In the method for producing organic molecules having at least two carbon atoms chained together by the reaction of a hydrogen-containing source, a carbon-containing source and an optional nitrogen-containing source in the presence of a nanostructure or nanostructures of present invention, the reaction is initiated by heat.

On contrary to the conventional approach of simulating photosynthesis by using light energy as the energy input for the endothermic reaction, the inventors found that, the artificial photosynthesis reaction can be initiated by heat in a dark environment. After the reaction is initiated, the reaction can continue to progress in the dark environment with the thermal energy of a heat source.

The term "heat" used herein refers to thermal energy transferred from one system to another as a result of thermal interactions. Heat may be transferred externally into the reaction with an external heat source. Alternatively, heat may be inherently carried by one component of the reaction so as to be transferred to other components involved in the reaction. In other words, the one component that inherently carries heat is an internal heat source.

In certain embodiments, the heat which initiates the reaction is input externally into the reaction, or is inherently carried by one or more of the hydrogen-containing source, the carbon-containing source and the optional nitrogen-containing source. Preferably, the heat is inherently carried by the carbon-containing source.

In preferred embodiments, the temperature of the catalyst, the carbon-containing source and the hydrogen-containing source is solely raised by a heat source during the reaction. That is to say, temperature of the reaction system is not raised by another energy source, such as light source.

The term "light" used herein refers to electromagnetic wave having a wavelength from about 250 nm to about 1000 nm. In other words, light refers to the irradiance of visible light.

The term "dark environment" used herein refers to an environment with substantially no incoming or incident light. For example, a dark environment is an environment having no light sources irradiating therein that has a radiation intensity capable of initiating a photosynthesis reaction. Moreover, the dark environment has substantially no incoming or incident light transmitting through the boundary between the dark environment and its surrounding.

Alternatively, in a dark environment with substantially no incoming or incident light, the light irradiation intensity within the environment is not capable of increasing the temperature of the reaction system, which means the irradiation intensity is close to zero.

Specifically, the light radiation intensity at any location within a dark environment is below 1 $W/cm^2$, preferably below 1 $mW/cm^2$, and most preferably below 1 $\mu W/cm^2$.

In preferred embodiments, the reaction of the present application is initiated in a dark environment as perceived by a skilled person in the art. For example, a curtained container, a closed pipeline or a dark room can be regarded as a dark environment according to the present invention. After initiation, the reaction continues to progress in a dark environment.

In another embodiment, after initiation of the reaction, the reaction is progressed under light. Preferably during the reaction of the present invention, the light radiation intensity is lower than the solar irradiance energy (e.g., solar constant). For example, the light radiation intensity is below 1000 $W/m^2$, preferably below 500 $W/m^2$, more preferably below 100 $W/m^2$. In preferred embodiments, the radiation, intensity of the light raises the temperature of the reaction system for 5° C. or less, more preferably for 1° C. or less. Most preferably, the reaction of the present application is also progressed in a dark environment with substantially no light. It should be understood that light will not inhibit the reaction of the present invention and the production of organic compounds in the presence of nanostructure catalyst is capable to progress under any light intensity.

In certain embodiments, the reaction is initiated under a temperature between about 20° C. to about 800° C., about 30° C. to about 300° C. about 50° C. to about 250° C., about 70° C. to about 200° C., about 80° C. to about 180° C., about 100° C. to about 150 about 110° C. to about 130° C., or any temperature within above ranges. Within a certain temperature range, raising the temperature leads to a higher yield of the hydrocarbon molecule products. The hydrocarbon molecule product of the catalyzed reaction is temperature-dependent.

The reaction period is not particularly limited in the present invention as long as the organic molecules are produced. The reaction can be a continuous reaction or an intermittent reaction. In other words, the reaction can be repeatedly initiated and terminated according to actual needs. With a well-established apparatus, the reaction is continuously performed with a continuous feed of heat and reaction materials.

Reaction Materials

In the reaction of the present invention, the reaction materials comprise a hydrogen-containing source, a carbon-containing source and an optional nitrogen-containing source.

The carbon-containing source is selected from the group consisting of $CO_2$, CO, $C_{1-4}$ hydrocarbons, $C_{1-4}$ alcohols, synthesis gas, bicarbonate salts and any combination thereof, or air, industrial flue gas, exhausts or emissions comprising one or more of these carbon-containing sources. The preferable carbon-containing source is $CO_2$ and CO.

The hydrogen-containing source is selected from the group consisting of water, $H_2$, $C_{1-4}$ hydrocarbons, $C_{1-4}$ alcohols and any combination thereof in liquid or gaseous phase, or waste water, industrial flue gas, exhausts or emissions comprising one or more of these hydrogen-containing sources. The preferable hydrogen-containing source is water.

The nitrogen-containing source is selected from the group consisting of $N_2$, air, ammonia, nitrogen oxides, nitro compounds, $C_{1-4}$ amines and any combination thereof in liquid or gaseous phase, or air, industrial flue gas, exhausts or emissions comprising one or more of these nitrogen-containing sources. The preferable nitrogen-containing source is ammonia and air.

For the purposes of recycling and treatment of industrial wastes, waster water, flue gas, combustion emission and automobile exhaust which contains the hydrogen-containing source, the carbon-containing source and the nitrogen-containing source can be used as the reaction material of the present invention.

As is commonly known, industrial wastes, especially flue gas from fossil fuel-fired electric power plant comprises a but amount of $CO_2$, $H_2O$ and latent heat. As described in the foregoing, $CO_2$, $H_2O$ and heat are essential components in the reaction of the present invention. The method of the present invention is particularly useful in recycling the material and thermal energy contained in the emission waste with the help of the nanostructure catalyst. Moreover, other components in the industrial waste that is usually considered as environment pollutants, such as nitrogen oxides, are also useful as reaction materials in the method of the present invention.

Reaction Products

The reaction of the present invention is capable to produce organic molecules having at least two carbon atoms chained together. The organic molecules comprise saturated, unsaturated and aromatic hydrocarbons, carbohydrates, amino acids, polymers, or a combination thereof.

Preferably, when the reaction material comprises a hydrogen-containing source and a carbon-containing source, the reaction product comprises long-chain hydrocarbon molecules and carbohydrates. When a nitrogen-containing source is further included in the reaction, the product can be amino acids or other polymers having nitrogen atoms in the structure.

In certain embodiments, the reaction product, such as hydrocarbon molecule produced by the catalyzed reaction, is temperature-dependent. In one preferred embodiment, saturated hydrocarbon molecules are more likely to be produced at low temperature; unsaturated and branched hydrocarbon molecules are more likely to be produced at intermediate temperature; and aromatic hydrocarbon molecules are more likely to be produced at high temperature. For example, in order to obtain fuel-like hydrocarbon molecules, the temperature is preferred to be between about 70° C. to about 200° C.

Method for Producing Organic Molecules

A method for producing organic molecules having at least two carbon atoms chained together is provided in the present invention. The method comprises the following steps:

contacting a nanostructure or nanostructures with at least a hydrogen-containing source, and a carbon-containing source;

heating the nanostructure or nanostructures, the hydrogen-containing source, and the carbon-containing source in a dark environment with substantially no light to initiate the reaction; and continuing the heating for the progression of the reaction to produce organic molecules.

In certain embodiments, an optional nitrogen-containing source is included in the reaction system.

Aspects of the method of the present invention has been detailed described in the foregoing contents, which will be more apparent to the skilled in the art upon reading the following preferred embodiments of the present invention.

EXAMPLES

Example 1. Carbon Isotopic Labeling with $^{12}CO_2$ and $^{13}CO_2$ 2 g of catalyst cobalt nanoparticle was loaded in each of two glass reactors (20 ml), and 350 mg of distilled water were added into each reactor to immerse the catalyst. The cobalt nanoparticles have a nearly spherical shape with a diameter of about 200 nm to 300 nm. Afterwards, each of the reactors was filled with 70 mg of $^{12}CO_2$ or $^{13}CO_2$, respectively, and was sealed. The reactors were then placed in an oven with a temperature set at 120° C. The oven has a stainless steel outer casing with a glass observation window mounted on the door. Observation window of the oven was shaded with multiple layers of aluminum foil and the interior lighting was kept off during reaction in order to create a dark environment. After heating for a period of 20 h, the reactors were removed from the oven and cooled to room temperature. Approximately 3 mL of dichloromethane (DCM) was injected into each reactor and shaken for ~10 min in order to extract non-volatile organic products. The DCM extracts were then analyzed by GC-MS.

As shown in FIGS. 1a and 1b, the total ion chromatogram from GC-MS reveals that a suite of $C_5$ to $C_{17}$ alkanes (straight saturated long-chain hydrocarbons, i.e., pentane ($C_5H_{12}$) to heptadecane ($C_{17}H_{36}$) was obtained from the artificial photosynthesis reaction in both samples. As an example, FIGS. 2a and 2b each illustrates the mass spectrum of the heptane ($C_7H_{16}$) obtained from the sample using $^{12}CO_2$ and $^{13}CO_2$, respectively.

Figure 2:
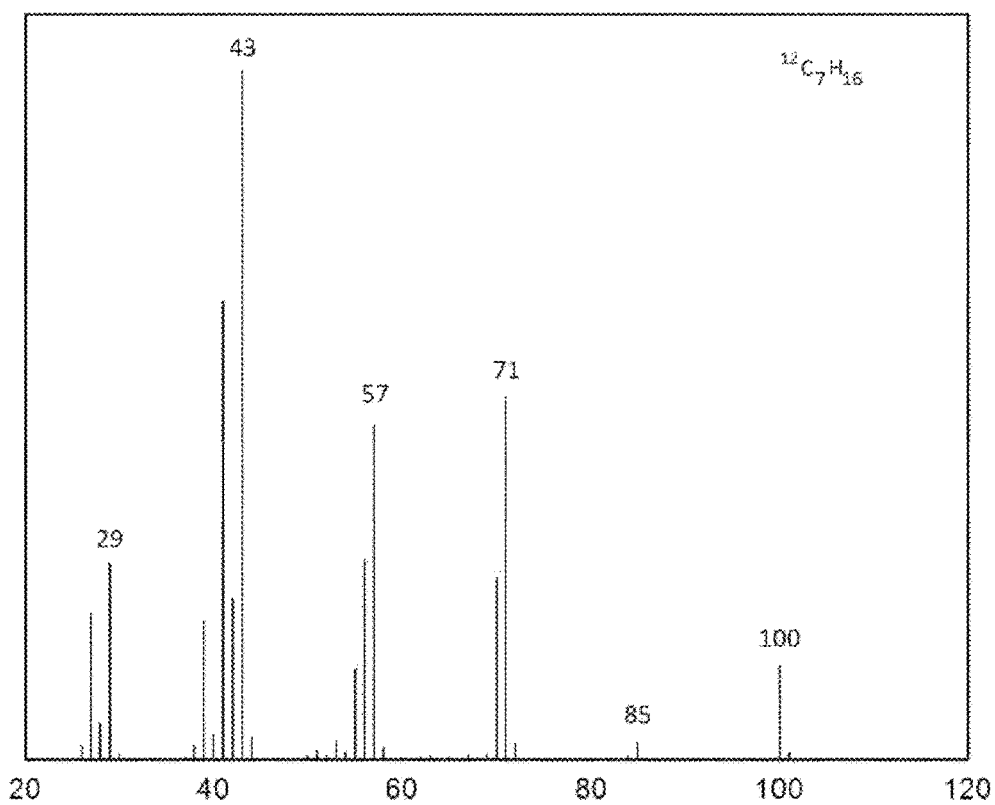
FIG. 2. Mass spectrum of the heptane ($C_7H_{16}$) obtained from the sample using $^{12}CO_2$ and $^{13}CO_2$.
Figure 2:
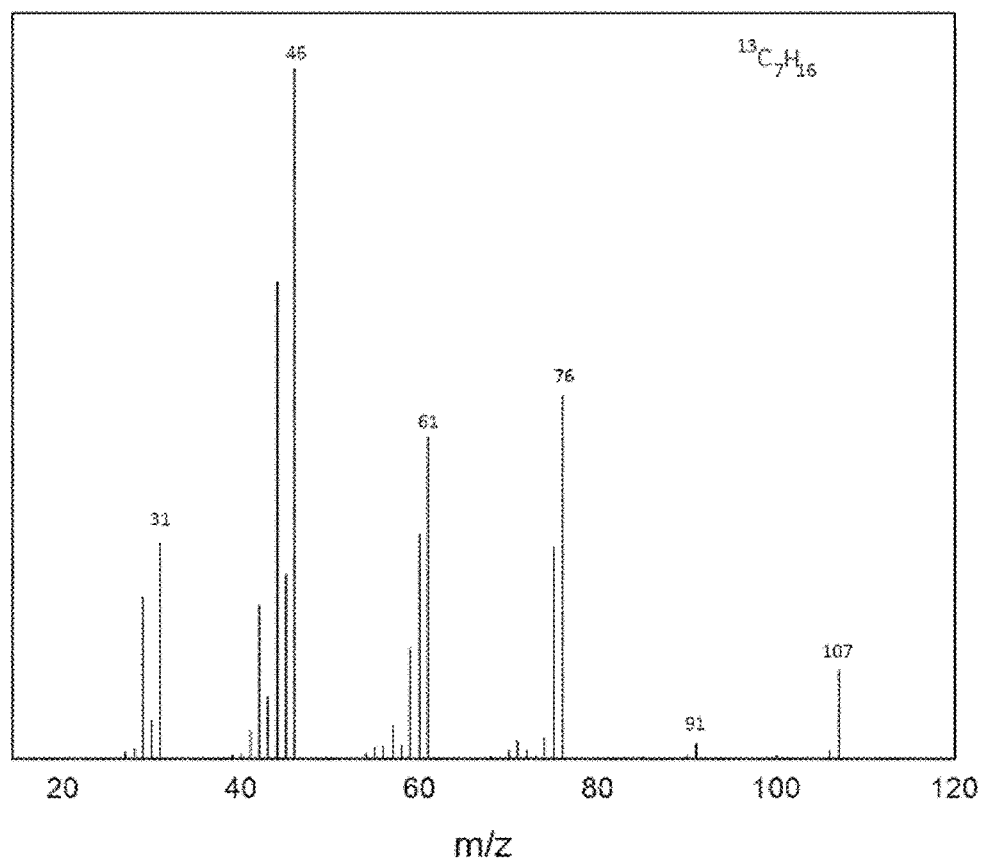

In FIG. 2a, wherein the carbon-containing source is $^{12}CO_2$, it shows that the molecular ion peak is at m/z=100

(corresponding to $^{12}C_7H_{16}^+$), and fragments ions peaks are at 29, 43, 57, 71, and 85 (respectively corresponding to $^{12}C_2H_5^+$, $^{12}C_3H_7^+$, $^{12}C_4H_9^+$, $^{12}C_5H_{11}^+$ and $^{12}C_6H_{13}^+$). In FIG. 2b, wherein the carbon-containing source is $^{13}CO_2$, it shows that the molecular ion peak is at m/z=107 (corresponding to $^{13}C_7H_{16}^+$), and fragment ion peaks are at 31, 46, 61, 76, and 91 (respectively corresponding to $^{13}C_2H_5^+$, $^{13}C_3H_7^+$, $^{13}C_4H_9^+$, $^{13}C_5H_{11}^+$ and $^{13}C_6H_{13}^+$). It is therefore demonstrated that all the alkanes synthesized during the experiments were products from the $CO_2$ in the reactors, with no contribution from background contaminants.

Example 2. Hydrogen Isotope Labeling with $H_2O$ and $D_2O$

Two additional experiments were conducted according to the method of Example 1 except that 350 mg of pure $H_2O$ and $D_2O$ are respectively added instead of distilled water, and without isotope labeling of $CO_2$. The DCM extracts were also analyzed by GC-MS.

Figure 3:
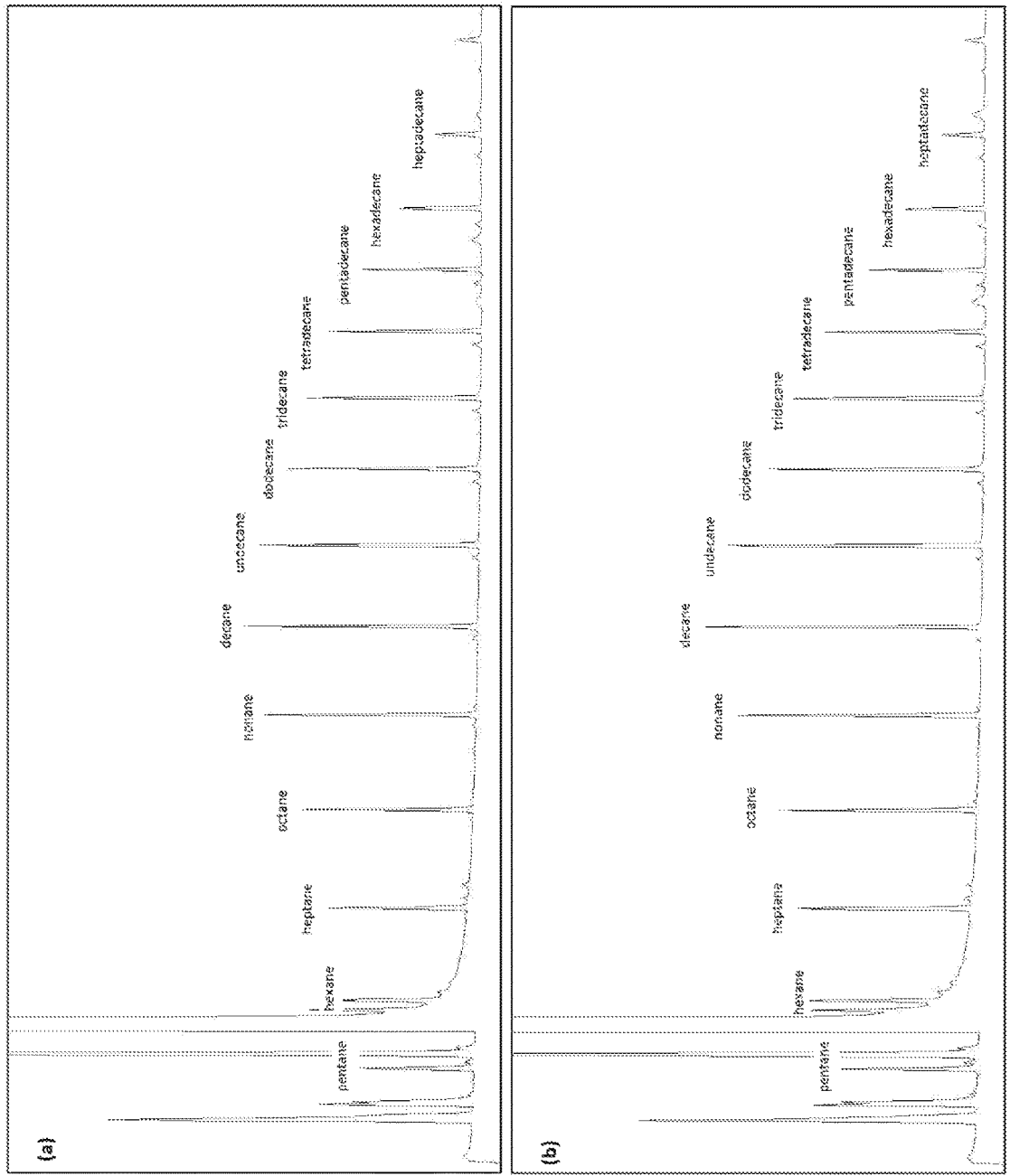
FIG. 3. Gas chromatography of hydrocarbons produced with $H_2O$ and $D_2O$ after 20 h of heating.
Figure 4:
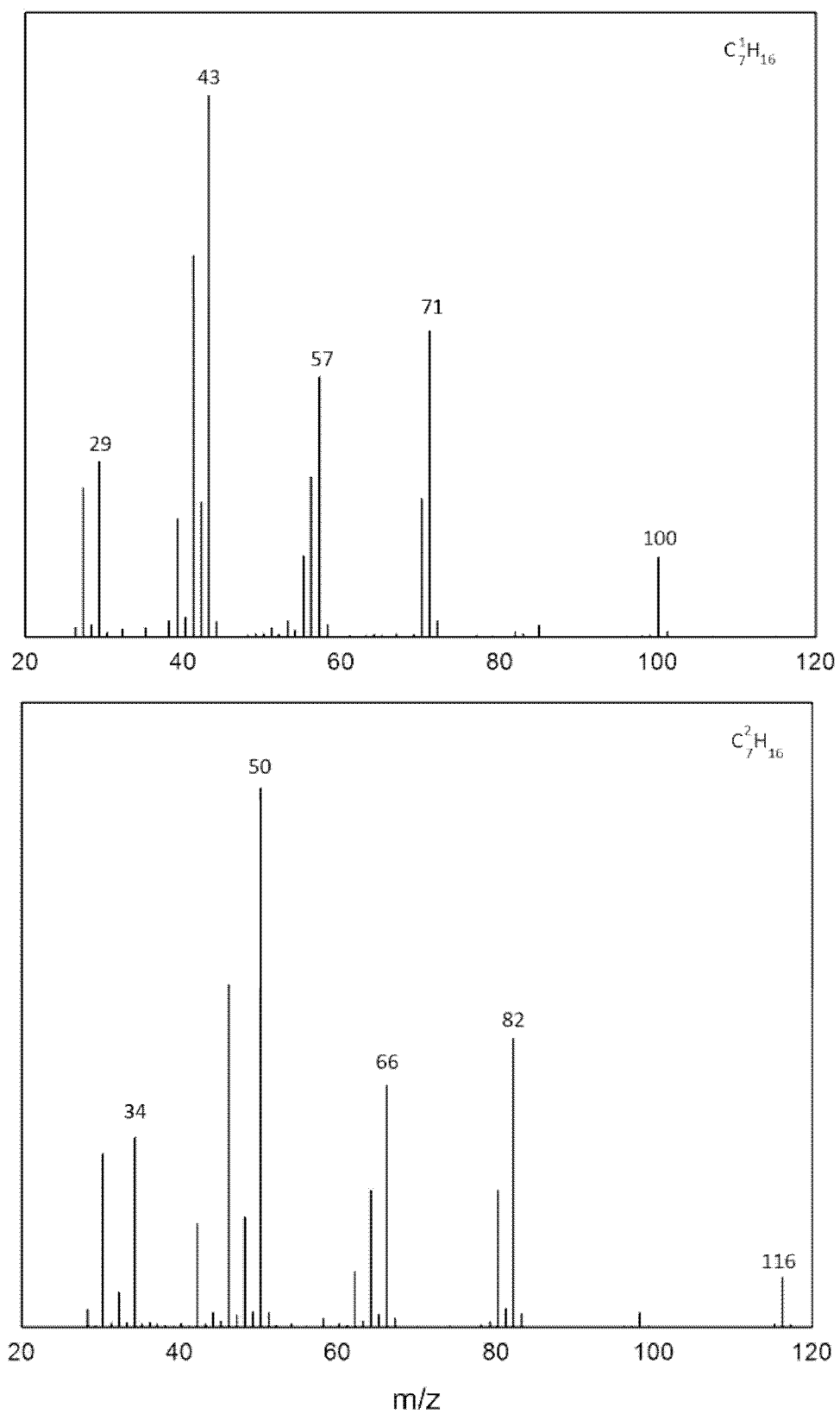
FIG. 4. Mass spectrum of the heptane ($C_7H_{16}$) obtained from the sample using $H_2O$ and $D_2O$.

The total ion chromatogram from GC-MS of the samples using $H_2O$ and $D_2O$ as reactant are shown in FIGS. 3a and 3b, respectively, indicating that a suite of $C_5$ to $C_{17}$ alkanes (straight saturated long-chain hydrocarbons, i.e., pentane ($C_5H_{12}$) to heptadecane ($C_{17}H_{36}$)) was obtained in both samples. FIGS. 4a and 4b each illustrates the mass spectrum of the heptane ($C_7H_{16}$) obtained from the sample using $H_2O$ and $D_2O$ as reactants, respectively.

In FIG. 2a, wherein the hydrogen-containing source is source is $H_2O$, it shows that the molecular ion peak is at m/z=100 (corresponding to $C_7H_{16}^+$), and fragments ions peaks are at 29, 43, 57, 71, and 85 (respectively corresponding to $C_2H_5^+$, $C_3H_7^+$, $C_4H_9^+$, $C_5H_{11}^+$ and $C_6H_{13}^+$). In FIG. 2b, wherein the hydrogen-containing source is $D_2O$, it shows that the molecular ion peak is at m/z=116 (corresponding to $C_7D_{16}^+$), and fragment ion peaks are at 34, 50, 66, 82, and 98 (respectively corresponding to $C_2D_5^+$, $C_3D_7^+$, $C_4D_9^+$, $C_5D_{11}^+$ and $C_6D_{13}^+$). It is therefore demonstrated that all the alkanes synthesized during the experiments were products from the $H_2O$ or $D_2O$ in the reactors, with no contribution from background contaminants.

Example 3. Production Output at Different Heating Temperature

Figure 5:
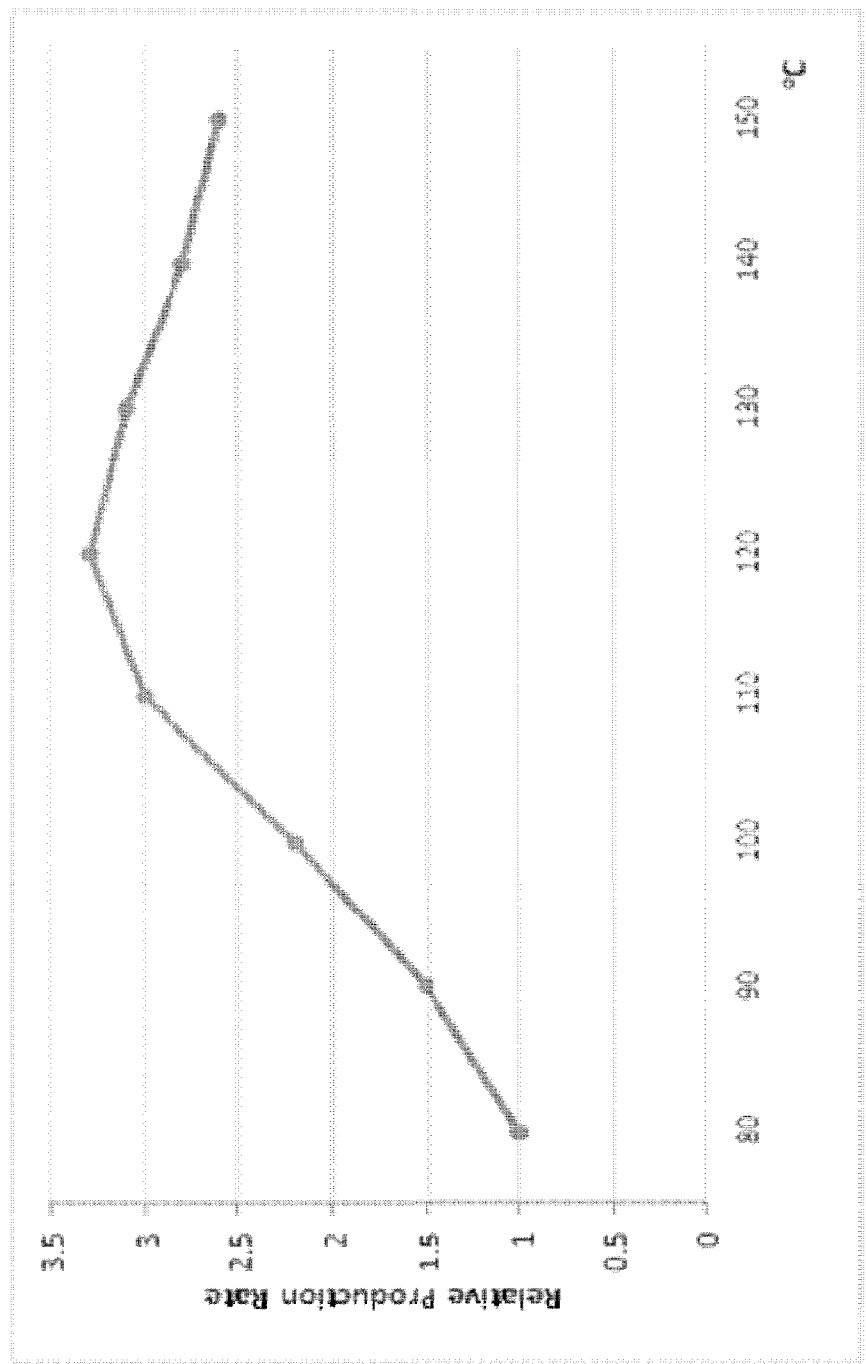
FIG. 5. Production output of the reaction at different heating temperatures.

The relationship between the amount of the products and the heating temperature was analyzed with 8 parallel experiments using the same reactant materials and catalyst with the apparatus of Example 1, heating for a same duration at different heating temperatures of 80° C., 90° C., 100° C., 110° C. 120° C., 130° C., 140° C. and 150° C. The production output of the reaction was measured by a GC-FID. The result is shown in FIG. 5.

As can be seen, the production output has a peak value at 120° C. within the tested temperature range from 80° C. to 150° C. The production output increases upon raising the reaction temperature from 80° C. to 120° C. At temperatures higher titan 120° C., the production output drops gradually.

Further experiment shows that the production output increases again when the heating temperature is higher than 180° C.; the products also start to change after 180° C. The proportion of straight saturated hydrocarbons production is decreased and the proportion of unsaturated hydrocarbons are increased. From 200° C. to 300° C., the aromatic hydrocarbons were identified as the main products. At higher temperature range, such as from 300° C. to 800° C., the products are the mixture of saturated, unsaturated and aromatic hydrocarbons.

Example 4. Performance of Other Nanostructure Catalysts

Additional experiments were performed with the apparatus of Example 1 using $H_2O$ and $CO_2$ as reactants. The following nanosticture catalysts was tested: CoO nanoparticles; mixture of Co nanoparticles and CoO nanoparticles; $MnO_2$ nanoparticles; Fe nanoparticles; FeO nanoparticles; mixture of Fe nanoparticles and FeO nanoparticles; stainless steel nanoparticles (i.e., Fe nanoparticles comprising impurities such C, Ni, and Cr); Co nanospikes deposited on Au substrate; mixture of $Co_2O_3$ nanoparticles and $Co_3O_4$ nanoparticles; mixture of Ag nanoparticles and CoO nanoparticles; mixture of Ag/Al/CoO nanoparticles. The above nanoparticles have a size (length/width/height) within the range of about 100 nm to 800 nm; the nanospikes have a conical shape with a height, of about 500 nm to 2000 nm and a thickness of less than 500 nm.

In all of above experiments, saturated hydrocarbon having more than 7 carbon atoms were produced as tested with GC-MS.

Among the above-mentioned nanostructure catalysts, from the standpoint of reaction efficiency, the most preferable catalysts are selected from the following: Co nanoparticles have a nearly spherical shape with a diameter of about 200 nm to 300 nm; Co nanospikes deposited on Au substrate, the nanospikes having a height of about 1000 nm to 2000 nm and a thickness of 200 to 500 nm; mixture of Co nanoparticles and CoO nanoparticles each having dimension of about 200 nm to 400 nm; and mixture of Fe nanoparticles and FeO nanoparticles each having dimension of about 200 nm to 400 nm.

Example 5. Production of Organic Molecules from Industrial Flue Gas

A simulated flue gas comprising $CO_2$, CO, $NO_2$, $H_2O$, and air and having an inherent temperature of 200° C. was continuously introduced into a reactor containing nanostructure catalyst of Cobalt nanoparticles and water. The reactor was configured as a dark environment for the reaction. Temperature inside the reactor was raised and maintained by the hot flue gas stream at about 130° C. to 140° C.

The reaction was terminated after 10 h and DCM was used to extract organic products from the liquid phase after the reactor was cooled down. The reaction product was analyzed by GC-MS. Saturated hydrocarbon molecules (i.e., alkanes) are the major product while other organic molecules such as unsaturated hydrocarbons (e.g., alkenes, alkynes, aromatic hydrocarbons) carbohydrates and amino acids also exists in trace amount.

In this specification and the appended claims, the singular forms "a", "an", and the include plural reference, unless the context clearly indicates otherwise. Unless defined otherwise, all technical and scientific terms used herein have the same meaning as commonly understood to one of ordinary skill in the art. Methods recited herein may be carried out in any order that is logically possible, in addition to a particular order disclosed.

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A method for producing organic molecules having at least two carbon atoms chained together by the reaction of a hydrogen-containing source, a carbon-containing source and an optional nitrogen-containing source in the presence of a nanostructure or nanostructures, wherein the reaction is initiated by heat in a dark environment,
wherein carbon-containing source is selected from the group consisting of $CO_2$ and CO, or air, industrial flue gas, exhausts, or emissions comprising one or more of $CO_2$ and CO,
wherein the hydrogen-containing source is water in liquid or gaseous phase, or waste water, industrial flue gas, exhausts, or emissions comprising water,
wherein the nitrogen-containing source is $NO_2$, or air, industrial flue gas, exhausts, or emissions comprising $NO_2$, and
the nanostructure each independently comprises a metal selected from the group consisting of Au, Al, Ag, Co, Fe, Ti, stainless steel, and any combination thereof, or the nanostructure each independently comprises a first component, a second component, or any combination thereof, wherein the first component is selected from the group consisting of Co, Fe, Al, Ag, Au, Zn, Ti, C, and any combination thereof, the second component is selected from the group consisting of Co, Ag, Rh, Pd, Os, Ir, La, Ce, oxides thereof, hydroxides thereof, inorganic acid salts thereof, C, and any combination thereof.

2. The method according to claim 1, wherein the nanostructure each independently comprises Co, wherein the first component is selected from the group consisting of Co, Ag, Au, C, and any combination thereof, the second component is selected from the group consisting of Co, oxides thereof and any combination thereof.

3. The method according to claim 2, wherein the first component and the second component are in contact with each other or apart from each other by a distance less than about 200 nm.

4. The method according to claim 1, wherein the nanostructure each independently is from about 1 nm to about 3000 nm in length, width or height.

5. The method according to claim 1, wherein the nanostructure each independently has a shape of spherical, spike, flake, needle, grass, cylindrical, polyhedral, 3D cone, cuboidal, sheet, hemispherical, irregular 3D shape, porous structure or any combinations thereof.

6. The method according to claim 1, wherein multiple nanostructures are arranged in a patterned configuration, in a plurality of layers, on a substrate, or randomly dispersed in a medium.

7. The method according to claim 1, wherein the organic molecules comprise saturated, unsaturated and aromatic hydrocarbons, carbohydrates, amino acids, polymers, or a combination thereof.

8. The method according to claim 1, wherein the heat provides a reaction temperature of between about 50° C. and about 800° C.

9. The method according to claim 1, wherein the heat is input externally into the reaction or is inherently carried by one or more of the hydrogen-containing source, the carbon-containing source and the optional nitrogen-containing source.

10. The method according to claim 1, wherein the carbon-containing source is $CO_2$.

11. The method according to claim 1, wherein the hydrogen-containing source is water.

12. The method according to claim 1, wherein the nitrogen-containing source is $NO_2$.

13. The method according to claim 1, wherein the heat is inherently carried by the carbon-containing source.

14. The method according to claim 1, wherein the nanostructure each independently consists of a metal selected from the group consisting of Au, Al, Ag, Co, Fe, Ti, stainless steel, and any combination thereof, or the nanostructure each independently consists of a first component, a second component, or any combination thereof, wherein the first component is selected from the group consisting of Co, Fe, Al, Ag, Au, Zn, Ti, C, and any combination thereof, the second component is selected from the group consisting of Co, Ag, Rh, Pd, Os, Ir, La, Ce, oxides thereof, hydroxides thereof, inorganic acid salts thereof, C, and any combination thereof.

* * * * *